(12) United States Patent
Kiener et al.

(10) Patent No.: US 8,518,264 B2
(45) Date of Patent: Aug. 27, 2013

(54) METHOD OF USING A METAL ORGANIC FRAMEWORKS BASED ON ALUMINUM FUMARATE

(75) Inventors: Christoph Kiener, Weisenheim am Sand (DE); Ulrich Müller, Neustadt (DE); Markus Schubert, Ludwigshafen (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/347,212

(22) Filed: Jan. 10, 2012

(65) Prior Publication Data

US 2012/0167761 A1 Jul. 5, 2012

Related U.S. Application Data

(62) Division of application No. 12/297,666, filed as application No. PCT/EP2007/053567 on Apr. 12, 2007, now abandoned.

(30) Foreign Application Priority Data

Apr. 18, 2006 (EP) ..................................... 06112713

(51) Int. Cl.
B01D 15/00 (2006.01)
(52) U.S. Cl.
USPC .............. 210/660; 210/600; 210/690; 95/139
(58) Field of Classification Search
USPC ....... 95/139; 428/304.4; 556/170; 134/6–7; 210/600, 660, 690
See application file for complete search history.

(56) References Cited

U.S. PATENT DOCUMENTS

| 6,666,666 | B1 | 12/2003 | Gilbert et al. |
| 6,929,679 | B2 | 8/2005 | Muller et al. |
| 2004/0081611 | A1 | 4/2004 | Muller et al. |
| 2006/0210458 | A1 | 9/2006 | Mueller et al. |
| 2007/0227898 | A1 | 10/2007 | Muller et al. |
| 2007/0248852 | A1 | 10/2007 | Mueller et al. |
| 2008/0190289 | A1 | 8/2008 | Muller et al. |

FOREIGN PATENT DOCUMENTS

| CA | 2620113 A1 | 3/2007 |
| DE | 102005000938 | 7/2006 |
| DE | 102005012087 | 9/2006 |
| DE | 102005022844 | 11/2006 |
| EP | 0102544 | 3/1984 |
| EP | 0200260 A2 | 12/1986 |
| EP | 0389041 A1 | 9/1990 |
| EP | 0576695 A1 | 1/1994 |
| EP | 0592050 A1 | 4/1994 |
| EP | 1674555 A1 | 6/2006 |
| EP | 1785428 A1 | 5/2007 |
| JP | 03-037156 | 2/1991 |
| JP | 06220067 A | 8/1994 |
| JP | 2000-109485 A | 4/2000 |
| WO | WO-94/29408 A1 | 12/1994 |
| WO | WO-95/19222 A1 | 7/1995 |
| WO | WO-03/035717 | 5/2003 |
| WO | WO-03/064030 | 8/2003 |
| WO | WO-03/101975 | 12/2003 |
| WO | WO-03/102000 A1 | 12/2003 |
| WO | WO-2004/013584 | 2/2004 |
| WO | WO-2004/037895 | 5/2004 |
| WO | WO-2005/003069 | 1/2005 |
| WO | WO-2005/003622 | 1/2005 |
| WO | WO-2005/049484 A1 | 6/2005 |
| WO | WO-2005/049892 A1 | 6/2005 |
| WO | WO-2006/072573 | 7/2006 |
| WO | WO-2006/089908 | 8/2006 |
| WO | WO-2007/023134 A1 | 3/2007 |
| WO | WO-2007/113118 A1 | 10/2007 |
| WO | WO-2008/062034 A1 | 5/2008 |
| WO | WO-2008/122542 A2 | 10/2008 |

OTHER PUBLICATIONS

A.J. Fletcher, et al., "Flexibility in metal-organic framework materials: Impact on sorption properties," *Journal of Solid State Chemistry*, (2005), pp. 2491-2510, vol. 178.

K. Seki, et al., "Syntheses and Characterization of Microporous Coordination Polymers with Open Frameworks," *J. Phys. Chem.*, (2002), pp. 1380-1385, vol. B, No. 106.

S. Kitagawa, et al., "Functional Porous Coordination Polymers," *Angew. Chem. Int.*, (2004), pp. 2334-2375, vol. 43.

S.C. Manna, et al., "Carboxylato-bridged 3D polymeric networks of GD(III): Synthesis, crystal structure, magnetic property and thermal behavior," *Polyhedron*, (2006), pp. 1779-1786, vol. 25.

T. Loiseau, et al., "A Rationale for the Large Breathing of the Porous Aluminum Terephthalate (MIL-53) Upon Hydration," *Chem. Eur. J.*, (2004, pp. 1373-1382, vol. 10.).

T. Loiseau, et al., "Hydrothermal synthesis and crystal structure of a new three-dimensional aluminum-organic framework MIL-69 with 2,6-naphthalenedicarboxylate (ndc), Al(OH)(ndc)•$H_2O$," *C.R. Chimie*, (2005), pp. 765-772, vol. 8.

W. Mori, et al., "Functional microporous materials of metal carboxylate: Gas-occlusion properties and catalytic activities," *Journal of Solid State Chemistry*, (2005), pp. 2555-2573. vol. 178.

W. Mori, et al., "Molecular-level design of efficient microporous materials containing metal carboxylates: inclusion complex formation with organic polymer, gas-occlusion properties, and catalytic activities for hydrogenation of olefins," *Microporous and Mesoporous Materials*, (2004), pp. 31-46, vol. 73.

Z. Shi, et al., "Coordination Polymers: Structural Transformation from Two to Three Dimensions through Ligand Conformation Change," *Inorg. Chem.*, (2000), pp. 1990-1993, vol. 39.

*Primary Examiner* — Christopher P Jones
(74) *Attorney, Agent, or Firm* — Novak Druce Connolly Bove + Quigg LLP

(57) ABSTRACT

A method comprising (i) providing a metal organic framework formed by $Al^{III}$ ions to which fumarate ions are coordinated to produce a porous framework structure, (ii) bringing a substance into contact with the metal organic framework such that the substance is uptaken by the porous metal organic framework to provide storage of or controlled release of, the substance.

5 Claims, 4 Drawing Sheets

METHOD OF USING A METAL ORGANIC FRAMEWORKS BASED ON ALUMINUM FUMARATE

CROSS-REFERENCE TO RELATED APPLICATIONS

This application is a divisional of application Ser. No. 12/297,666 filed Oct. 29, 2008, now abandoned, which is incorporated by reference by its entirety, application Ser. No. 12/297,666 is a national stage application, under 35 U.S.C. §371, of PCT/EP2007/053567, filed Apr. 12, 2007, which claims priority of European Patent Application No. 06112713.0, filed Apr. 18, 2006.

BACKGROUND OF THE INVENTION

The present invention relates to a porous metal organic framework, shaped bodies comprising this, a process for preparing the framework and its use.

Porous metal organic frameworks are known from the prior art. They are distinguished, in particular, by their porosity and can frequently be employed in applications comparable to those which are known for inorganic zeolites.

Metal organic frameworks usually comprise an at least bidentate organic compound coordinated to a metal ion to form the skeleton of the metal organic framework.

An appropriate choice of metal and/or organic compound makes it possible to optimize the framework for the desired field of application. For example, the choice of the organic compound can exert an influence on the pore distribution. In addition, the metal can make a contribution in adsorption processes.

There is thus a continual need to provide specific metal organic frameworks which, in particular, have extraordinary properties attributable to the choice of the metal and of the organic compound.

BRIEF SUMMARY OF THE INVENTION

The present invention relates to a porous metal organic framework, shaped bodies comprising this, a process for preparing the framework and its use.

One interesting metal is aluminum since comparatively robust metal organic frameworks can be obtained as a result of strong coordinate bonds. In addition, the aluminum ion is, due to its octahedral coordination, in principle capable of building up three-dimensional framework compounds. Furthermore, the salts of aluminum used as starting materials are readily available and inexpensive.

It is therefore an object of the present invention to provide frameworks which are based on aluminum and have particular properties, especially in respect of the storage and separation of chemical substances such as gases.

The object is achieved by a porous metal organic framework formed by $Al^{III}$ ions to which fumarate ions are coordinated to produce a framework structure.

It has been found that the porous metal organic framework formed by aluminum ions and fumarate ions (trans-1,2-ethylenedicarboxylate) surprisingly has a one-dimensional channel structure which additionally displays a surprising high specific surface area, so that the metal organic framework of the present invention can be particularly useful for the storage and separation of chemical substances, in particular gases.

The porous metal organic framework of the invention thus has a one-dimensional channel structure which crystallizes in the orthorhombic system.

A BRIEF DESCRIPTION OF THE FIGURES

DETAILED DESCRIPTION OF THE INVENTION

The structure of the porous metal organic framework of the invention can be recognized, in particular, by the X-ray diffraction pattern (XRD) having a basic reflection in the range $8°<2\Theta<12°$.

Figure 1:
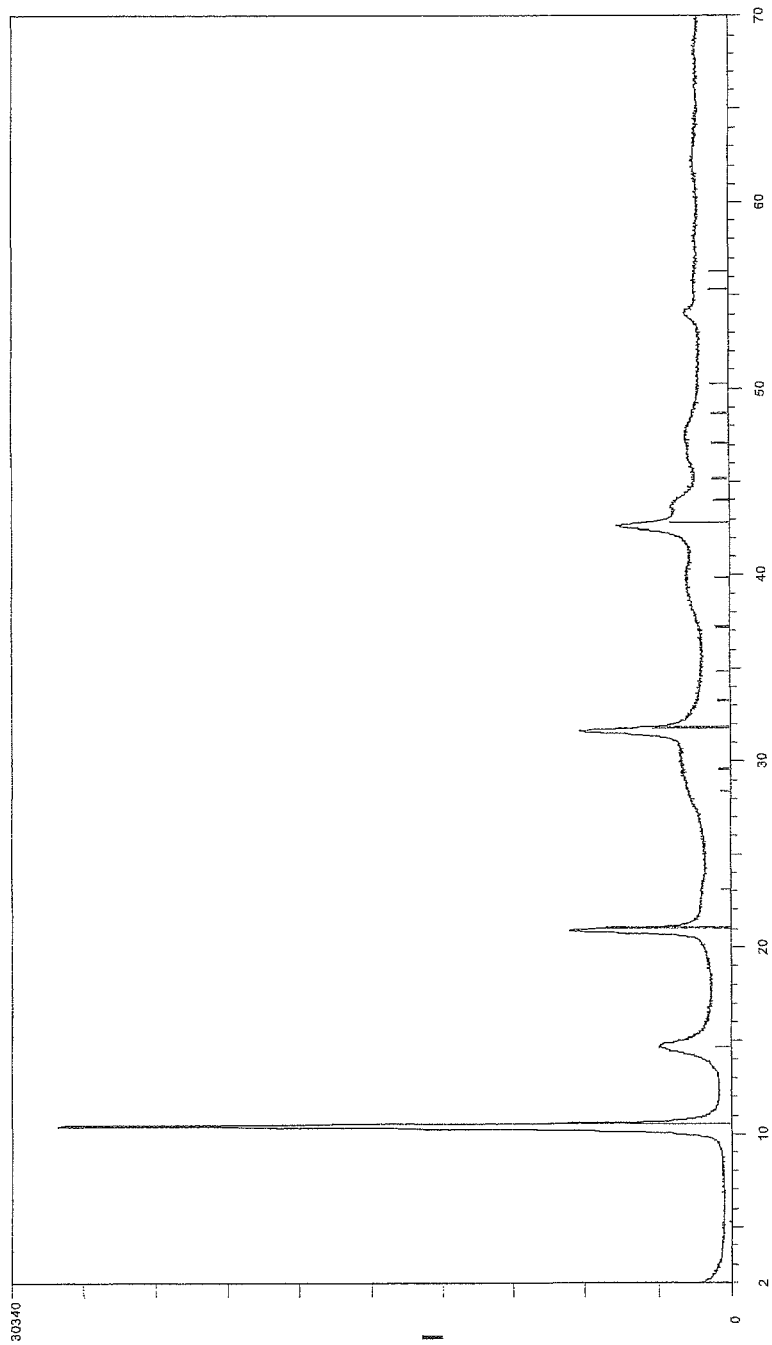
FIG. 1 shows the X-ray diffraction pattern of the porous metal organic framework of the invention. Here, the intensity I (Lin(counts)) is shown as a function of the 2 theta scale ($2\Theta$).

FIG. 1 shows the X-ray diffraction pattern of the porous metal organic framework of the invention. Here, the intensity I (Lin(counts)) is shown as a function of the 2 theta scale ($2\Theta$).

Here, the diffraction pattern can be recorded as follows: the sample is installed as a powder in the sample container of a commercially available instrument (Siemens D-5000 diffractometer or Bruker D8-Advance). Cu—K$\alpha$ radiation with variable primary and secondary apertures and secondary monochromator is used as radiation source. The signal is detected by means of a scintillation detector (Siemens) or Solex semiconductor detector (Bruker). The measurement range for $2\Theta$ is typically chosen as from 2° to 70°. The angle step is 0.02°, and the measurement time per angle step is typically from 2 to 4 seconds. In the evaluation, reflections are distinguished by a signal strength which is at least 3 times as high as the background noise. An area analysis can be carried out manually by drawing a baseline under the individual reflections. As an alternative, programs such as "Topas-Profile" from Bruker can be used, in which case the background smoothing then preferably occurs automatically via a 1st order polynomial in the software.

The framework of the invention has a one-dimensional channel structure in which linear chains of $Al^{III}$ ions and OH groups are bridged by the organic fumarate to give a three-dimensional, orthorhombic structure.

The metal organic framework of the invention can be present in powder form or as agglomerate.

The porous metal organic framework of the invention can be used as such in powder form or is converted into a shaped body.

Accordingly, a further aspect of the present invention is the porous metal organic framework of the invention in powder form.

A further aspect of the present invention is accordingly a shaped body comprising the porous metal organic framework of the invention.

The production of shaped bodies comprising metal organic frameworks is described, for example, in WO-A 03/102000.

Here, preferred processes for producing shaped bodies are extrusion and tableting. In the production of the shaped bodies, the framework can be present in a mixture with further materials, for example binders, lubricants or other additives, which are added during production. It is likewise conceivable for the framework to comprise further constituents, for example absorbents such as activated carbon or the like.

The possible geometries of the shaped bodies are essentially not subject to any restrictions. Examples which may be mentioned are, inter alia, pellets such as disk-shaped pellets, pills, spheres, granules, extrudates such as rods, honeycombs, grids or hollow bodies.

To produce these shaped bodies, it is in principle possible to employ all suitable methods. In particular, the following processes are preferred:

Kneading/pan milling of the framework either alone or together with at least one binder and/or at least one pasting agent and/or at least one template compound to give a mixture; shaping of the resulting mixture by means of at least one suitable method such as extrusion; optionally washing and/or drying and/or calcination of the extrudate; optionally finishing treatment.

Tableting together with at least one binder and/or another auxiliary.

Application of the framework to at least one optionally porous support material. The material obtained can then be processed further by the above-described method to give a shaped body.

Application of the framework to at least one optionally porous substrate.

Kneading/pan milling and shaping can be carried out by any suitable method, for example as described in Ullmanns Enzyklopädie der Technischen Chemie, 4th edition, volume 2, p. 313 ff. (1972).

For example, the kneading/pan milling and/or shaping can be carried out by means of a piston press, roller press in the presence or absence of at least one binder, compounding, pelletization, tableting, extrusion, coextrusion, foaming, spinning, coating, granulation, preferably spray granulation, spraying, spray drying or a combination of two or more of these methods.

Very particular preference is given to producing pellets and/or tablets.

The kneading and/or shaping can be carried out at elevated temperatures, for example in the range from room temperature to 300° C., and/or under superatmospheric pressure, for example in the range from atmospheric pressure to a few hundred bar, and/or in a protective gas atmosphere, for example in the presence of at least one noble gas, nitrogen or a mixture of two or more thereof.

The kneading and/or shaping is, in a further embodiment, carried out with addition of at least one binder, with the binder used basically being able to be any chemical compound which ensures the viscosity desired for the kneading and/or shaping of the composition to be kneaded and/or shaped. Accordingly, binders can, for the purposes of the present invention, be either viscosity-increasing or viscosity-reducing compounds.

Preferred binders are, for example, inter alia, aluminum oxide or binders comprising aluminum oxide, as are described, for example, in WO 94/29408, silicon dioxide as described, for example, in EP 0 592 050 A1, mixtures of silicon dioxide and aluminum oxide, as are described, for example, in WO 94/13584, clay minerals as described, for example, in JP 03-037156 A, for example montmorillonite, kaolin, bentonite, halloysite, dickite, nacrite and anauxite, alkoxysilanes as are described, for example, in EP 0 102 544 B1, for example tetraalkoxysilanes such as tetramethoxysilane, tetraethoxysilane, tetrapropoxysilane, tetrabutoxysilane, or, for example, trialkoxysilanes such as trimethoxysilane, triethoxysilane, tripropoxysilane, tributoxysilane, alkoxytitanates, for example tetralkoxytitanates such as tetramethoxytitanate, tetraethoxytitanate, tetrapropoxytitanate, tetrabutoxytitanate, or, for example, trialkoxytitanates such as trimethoxytitanate, triethoxytitanate, tripropoxytitanate, tributoxytitanate, alkoxyzirconates, for example tetralkoxyzirconates such as tetramethoxyzirconate, tetraethoxyzirconate, tetrapropoxyzirconate, tetrabutoxyzirconate, or, for example, trialkoxyzirconates such as trimethoxyzirconate, triethoxyzirconate, tripropoxyzirconate, tributoxyzirconate, silica sols, amphiphilic substances and/or graphites.

As viscosity-increasing compound, it is, for example, also possible to use, if appropriate in addition to the abovementioned compounds, an organic compound and/or a hydrophilic polymer such as cellulose or a cellulose derivative such as methylcellulose and/or a polyacrylate and/or a polymethacrylate and/or a polyvinyl alcohol and/or a polyvinylpyrrolidone and/or a polyisobutene and/or a polytetrahydrofuran and/or a polyethylene oxide.

As pasting agent, it is possible to use, inter alia, preferably water or at least one alcohol such as a monoalcohol having from 1 to 4 carbon atoms, for example methanol, ethanol, n-propanol, isopropanol, 1-butanol, 2-butanol, 2-methyl-1-propanol or 2-methyl-2-propanol or a mixture of water and at least one of the alcohols mentioned or a polyhydric alcohol such as a glycol, preferably a water-miscible polyhydric alcohol, either alone or as a mixture with water and/or at least one of the monohydric alcohols mentioned.

Further additives which can be used for kneading and/or shaping are, inter alia, amines or amine derivatives such as tetraalkylammonium compounds or amino alcohols and carbonate-comprising compounds such as calcium carbonate. Such further additives are described, for instance, in EP 0 389 041 A1, EP 0 200 260 A1 or WO 95/19222.

The order of the additives such as template compound, binder, pasting agent, viscosity-increasing substance during shaping and kneading is in principle not critical.

In a further preferred embodiment, the shaped body obtained by kneading and/or shaping is subjected to at least one drying step which is generally carried out at a temperature in the range from 25 to 500° C., preferably in the range from 50 to 500° C. and particularly preferably in the range from 100 to 350° C. It is likewise possible to carry out drying under reduced pressure or under a protective gas atmosphere or by spray drying.

In a particularly preferred embodiment, at least one of the compounds added as additives is at least partly removed from the shaped body during this drying process.

The metal organic framework of the invention comprises pores, in particular micropores and/or mesopores. Micropores are defined as pores having a diameter of 2 nm or less and mesopores are defined by a diameter in the range from 2 to 50 nm (Pure & Appl. Chem. 57 (1985) 603-619). The presence of micropores and/or mesopores can be checked by means of sorption measurements, with these measurements determining the uptake capacity of the metal organic frameworks for nitrogen at 77 kelvin (Langmuir method) in accordance with DIN 66131 and/or DIN 66134.

The pores are preferably present in the form of one-dimensional channels having a diameter of from 5 to 15 angström, particularly preferably from 7 to 12 Å.

The specific surface area, calculated according to the Langmuir model (DIN 66131, 66134), of the metal organic framework of the invention in powder form is preferably at least 1000 $m^2/g$, more preferably at least 1200 $m^2/g$, more preferably at least 1400 $m^2/g$, even more preferably at least 1600 $m^2/g$, even more preferably at least 1800 $m^2/g$ and particularly preferably at least 1950 $m^2/g$.

Shaped bodies comprising the metal organic framework of the invention can have a lower specific surface area, but preferably at least 500 m$^2$/g, more preferably at least 600 m$^2$/g, even more preferably at least 700 m$^2$/g, in particular at least 800 m$^2$/g.

The present invention further provides a process for preparing a porous metal organic framework according to the invention, which comprises the step reaction of a reaction mixture comprising at least one aluminum compound and fumaric acid or a salt thereof in the presence of an organic solvent at a predetermined temperature and a predetermined pressure.

The organic component of the porous metal organic framework of the invention is fumaric acid which can be reacted with an aluminum compound. It is likewise possible to use derivatives of fumaric acid. Thus, for example, it is conceivable to use fumaric acid in the form of its salt. The salt, in which fumaric acid is present as completely or partially deprotonated anion, can have any suitable cation.

Such cations can be, for example, monovalent or divalent, preferably monovalent, metal ions. Examples are, in particular, sodium and potassium salts. It is likewise possible to use cations of ammonium compounds. Here, particular mention may be made of ammonium itself and also alkylammonium cations.

The aluminum compound can be produced by anodic oxidation of metallic aluminum. In such a case the porous metal organic framework of the invention is prepared by an at least partly electrochemical route. Processes for the electrochemical preparation of porous metal organic frameworks are described in WO-A 2005/049892. The aluminum compound for the porous metal organic framework of the invention can also be produced by this route.

In the electrochemical preparation of the porous metal organic framework of the invention, preference is given to cathodic redeposition of the aluminum ion being at least partly prevented by means of at least one of the following measures:
(i) use of an electrolyte which promotes cathodic formation of hydrogen;
(ii) addition of at least one compound which leads to cathodic depolarization;
(iii) use of a cathode having a suitable hydrogen overvoltage.

The process can be carried out in an undivided electrolysis cell. Especially useful cells are gap cells or stacked plate cells. These can be connected in a bipolar fashion. Suitable reaction media are, for example, methanol, ethanol, dimethylformamide, diethylformamide or a mixture of two or more of these solvents.

An electrolyte salt or a plurality of electrolyte salts can also be present in the reaction mixture. Here, the electrolyte salt can have a quaternary ammonium ion as cation component and an alkoxysulfate ion as anion component. The total solids content should be greater than or equal to 0.5% by weight.

The reaction in the process of the invention for preparing the metal organic framework of the invention can also be carried out by a classical route. Here, the aluminum compound is typically an aluminum salt.

The aluminum salt can be present in the form of an alkoxide, acetonate, halide, sulfite, as a salt of an organic or inorganic, oxygen-comprising acid or a mixture thereof.

An alkoxide is, for example, a methoxide, ethoxide, n-propoxide, i-propoxide, n-butoxide, i-butoxide, t-butoxide or phenoxide.

An acetonate is, for example, acetylacetonate.

A halide is, for example, chloride, bromide or iodide.

An organic, oxygen-comprising acid is, for example, formic acid, acetic acid, propionic acid or another alkylmonocarboxylic acid.

An inorganic, oxygen-comprising acid is, for example, sulfuric acid, sulfurous acid, phosphoric acid or nitric acid.

More preferred aluminum compounds are inorganic aluminum salts such as aluminum chloride, aluminum bromide, aluminum hydrogensulfate, aluminum dihydrogen phosphate, aluminum monohydrogen phosphate, aluminum phosphate, aluminum nitrate.

The aluminum compound can, if appropriate, comprise water of hydration, which is preferred. Particularly preferred aluminum compounds are the hydrates of the chloride, nitrate and sulfate.

The reaction in the process of the invention for preparing the porous metal organic framework of the invention is carried out at least in the presence of an organic solvent. Here, solvothermal conditions can be used.

For the purposes of the present invention, the term "thermal" refers to a preparative process in which the reaction to form the porous metal organic framework of the invention is carried out in a pressure vessel which is closed during the reaction and to which elevated temperature is applied so that a pressure builds up within the reaction medium in the pressure vessel as a result of the vapor pressure of the solvent present.

The reaction preferably does not occur in a water-comprising medium and thus not under solvothermal conditions.

Accordingly, the reaction in the process of the invention preferably occurs in the presence of a nonaqueous solvent.

The reaction is preferably carried out at a pressure of from 1 bar to 16 bar (absolute), preferably from 1 to 3 bar (absolute). However, the pressure is more preferably not more than 1230 mbar (absolute). The reaction particularly preferably takes place at atmospheric pressure. However, slight superatmospheric or subatmospheric pressures can occur due to the apparatus. For the purposes of the present invention, the term "atmospheric pressure" therefore refers to the pressure range given by the actual atmospheric pressure±150 mbar.

The reaction preferably takes place in a temperature range from 100° C. to 200° C. The temperature is preferably in the range from 110° C. to 170° C. The temperature is more preferably in the range from 120° C. to 150° C.

The reaction mixture can further comprise a base. This serves, in particular, to ensure that when the carboxylic acid is used as at least bidentate organic compound, this is readily soluble. When an organic solvent is used, it is frequently not necessary to add such a base. Nevertheless, the solvent for the process of the invention can be selected so that it itself is basic, but this is not absolutely necessary for carrying out the process of the invention.

It is likewise possible to use a base. However, preference is given to no additional base being used.

Furthermore, it is advantageous for the reaction to be able to take place with stirring, which is also advantageous in a scale-up.

The (nonaqueous) organic solvent is preferably a $C_{1-6}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cyclic ketones such as cyclohexanone, sulfolene or mixtures thereof.

A $C_{1-6}$-alkanol is an alcohol having from 1 to 6 carbon atoms. Examples are methanol, ethanol, n-propanol, isopropanol, n-butanol, isobutanol, t-butanol, pentanol, hexanol and also mixtures thereof.

An optionally halogenated $C_{1-200}$-alkane is an alkane which has from 1 to 200 carbon atoms and in which one or more up to all hydrogen atoms can be replaced by halogen, preferably chlorine or fluorine, in particular chlorine. Examples are chloroform, dichloromethane, tetrachloromethane, dichloroethane, hexane, heptane, octane and mixtures thereof.

Preferred solvents are DMF, DEF, DMAc and NMP. Particular preference is given to DMF.

The term "nonaqueous" preferably refers to a solvent which does not exceed a maximum water content of 10% by weight, more preferably 5% by weight, even more preferably 1% by weight, more preferably 0.1% by weight, particularly preferably 0.01% by weight, based on the total weight of the solvent.

The maximum water content during the reaction is preferably 10% by weight, more preferably 5% by weight and even more preferably 1% by weight.

The term "solvent" encompasses pure solvents and mixtures of various solvents.

Furthermore, the process step of reaction of the at least one metal compound with the at least one at least bidentate organic compound is preferably followed by a calcination step. The temperature set here is typically above 250° C., preferably from 300 to 400° C.

The at least bidentate organic compound present in the pores can be removed by means of the calcination step.

In addition or as an alternative thereto, the removal of the at least bidentate organic compound (ligand) from the pores of the porous metal organic framework can be effected by treatment of the framework formed with a nonaqueous solvent. Here, the ligand is removed in a type of "extraction process" and may be replaced by a solvent molecule in the framework.

The treatment is preferably carried out for at least 30 minutes and can typically be carried out for up to 7 days. This can occur at room temperature or elevated temperature. It preferably takes place at elevated temperature, for example at at least 40° C., preferably 60° C. The extraction more preferably takes place at the boiling point of the solvent used (under reflux).

The treatment can be carried out in a simple vessel by slurrying and stirring of the framework. It is also possible to use extraction apparatuses such as Soxhlet apparatuses, in particular industrial extraction apparatuses.

As suitable solvents, it is possible to use those mentioned above, i.e., for example, $C_{1-6}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cyclic ketones such as cyclohexanone or mixtures thereof.

Preference is given to methanol, ethanol, propanol, acetone, MEK and mixtures thereof.

A very particularly preferred extraction solvent is methanol.

The solvent used for the extraction can be identical to or different from that for the reaction of the at least one metal compound with the at least one at least bidentate organic compound. It is not absolutely necessary in the "extraction" but preferred that the solvent is water-free.

It is preferred that the molar ratio of aluminum compound to fumaric acid or one of its salts in the process of the invention is in the range from 0.3:1 to 1.7:1. The ratio is more preferably in the range from 0.7:1 to 1.2:1.

The present invention further provides for the use of a porous metal organic framework according to the invention for the uptake of at least one substance for the purposes of its storage, separation, controlled release, chemical reaction or as support.

The at least one substance is preferably a gas or a gas mixture. Liquids are also possible.

Processes for storage by means of metal organic frameworks in general are described in WO-A 2005/003622, WO-A 2003/064030, WO-A 2005/049484, WO-A 2006/089908 and DE-A 10 2005 012 087. The processes described there can also be used for the metal organic framework of the invention. Preferred gases for storage are methane or hydrogen.

Processes for separation or purification by means of metal organic frameworks in general are described in EP-A 1 674 555, DE-A 10 2005 000938 and the German patent application number DE-A 10 2005 022 844. The processes described there can also be used for the metal organic framework of the invention. A preferred gas to be separated off is carbon dioxide, in particular from a gas mixture which further comprises carbon monoxide.

If the porous metal organic framework of the invention is used for storage, this preferably takes place in a temperature range from −200° C. to +80° C. A greater preference is given to a temperature range from −40° C. to +80° C. A preferred pressure range is from 20 bar to 1000 bar (absolute), in particular from 100 bar to 400 bar.

For the purposes of the present invention, the terms "gas" and "liquid" are used in the interests of simplicity, but gas mixtures and liquid mixtures or liquid solutions are likewise encompassed by the term "gas" or "liquid", respectively.

Preferred gases are hydrogen, natural gas, town gas, hydrocarbons, in particular methane, ethane, ethene, acetylene, propane, n-butane and i-butane, carbon monoxide, carbon dioxide, nitrogen oxides, oxygen, sulfur oxides, halogens, halogenated hydrocarbons, $NF_3$, $SF_6$, ammonia, boranes, phosphanes, hydrogen sulfide, amines, formaldehyde, noble gases, in particular helium, neon, argon, krypton and xenon.

The gas is particularly preferably carbon dioxide which is separated off from a gas mixture comprising carbon dioxide. The gas mixture preferably comprises carbon dioxide together with at least $H_2$, $CH_4$ or carbon monoxide. In particular, the gas mixture comprises carbon dioxide together with carbon monoxide. Very particular preference is given to mixtures which comprise at least 10% by volume and not more than 45% by volume of carbon dioxide and at least 30% by volume and not more than 90% by volume of carbon monoxide.

A preferred embodiment is pressure swing adsorption using a plurality of parallel adsorber reactors, with the adsorbent bed consisting entirely or partly of the material of the invention. In the case of $CO_2/CO$ separation, the adsorption phase preferably takes place at a $CO_2$ partial pressure of from 0.6 to 3 bar and a temperature of at least 20° C. but not more than 70° C. To desorb the adsorbed carbon dioxide, the total pressure in the adsorber reactor concerned is usually reduced to values in the range from 100 mbar to 1 bar.

Preference is also given to the use of the framework of the invention for storage of a gas at a minimum pressure of 100 bar (absolute). The minimum pressure is more preferably 200 bar (absolute), in particular 300 bar (absolute). Here, the gas is particularly preferably hydrogen or methane.

However, the at least one substance can also be a liquid. Examples of such a liquid are disinfectants, inorganic or organic solvents, fuels, in particular gasoline or diesel, hydraulic fluids, radiator fluids, brake fluids or an oil, in particular machine oil. Furthermore, the liquid can be a halogenated aliphatic or aromatic, cyclic or acyclic hydrocarbon or a mixture thereof. In particular, the liquid can be acetone, acetonitrile, aniline, anisole, benzene, benzonitrile, bromobenzene, butanol, tert-butanol, quinoline, chlorobenzene, chloroform, cyclohexane, diethylene glycol, diethyl ether, dimethylacetamide, dimethylformamide, dimethyl sulfoxide, dioxane, glacial acetic acid, acetic anhydride, ethyl acetate, ethanol, ethylene carbonate, ethylene dichloride, ethylene glycol, ethylene glycol dimethyl ether, formamide, hexane, isopropanol, methanol, methoxypropanol, 3-methyl-1-butanol, methylene chloride, methyl ethyl ketone, N-methylformamide, N-methylpyrrolidone, nitrobenzene, nitromethane, piperidine, propanol, propylene carbonate, pyridine, carbon disulfide, sulfolane, tetrachloroethene, carbon tetrachloride, tetrahydrofuran, toluene, 1,1,1-trichloroethane, trichloroethylene, triethylamine, triethylene glycol, triglyme, water or a mixture thereof.

The at least one substance can also be an odorous substance.

The odorous substance is preferably a volatile organic or inorganic compound which comprises at least one of the elements nitrogen, phosphorus, oxygen, sulfur, fluorine, chlorine, bromine or iodine or an unsaturated or aromatic hydrocarbon or a saturated or unsaturated aldehyde or a ketone. More preferred elements are nitrogen, oxygen, phosphorus, sulfur, chlorine, bromine; and particular preference is given to nitrogen, oxygen, phosphorus and sulfur.

In particular, the odorous substance is ammonia, hydrogen sulfide, sulfur oxides, nitrogen oxides, ozone, cyclic or acyclic amines, thiols, thioethers and also aldehydes, ketones, esters, ethers, acids or alcohols. Particular preference is given to ammonia, hydrogen sulfide, organic acids (preferably acetic acid, propionic acid, butyric acid, isobutyric acid, valeric acid, isovaleric acid, caproic acid, heptanoic acid, lauric acid, pelargonic acid) and cyclic or acyclic hydrocarbons which comprise nitrogen or sulfur and also saturated or unsaturated aldehydes such as hexanal, heptanal, octanal, nonanal, decanal, octenal or nonenal and in particular volatile aldehydes such as butyraldehyde, propionaldehyde, acetaldehyde and formaldehyde and also fuels such as gasoline, diesel (constituents).

The odorous substances can also be fragrances which are used, for example, for producing perfumes. Examples of fragrances or oils which release such fragrances are: essential oils, basil oil, geranium oil, mint oil, cananga oil, cardamom oil, lavender oil, peppermint oil, nutmeg oil, Camilla oil, eucalyptus oil, rosemary oil, lemon oil, lime oil, orange oil, bergamot oil, muscatel sage oil, coriander oil, cypress oil, 1,1-dimethoxy-2-phenylethane, 2,4-dimethyl-4-phenyltetrahydrofuran, dimethyltetrahydrobenzaldehyde, 2,6-dimethyl-7-octen-2-ol, 1,2-diethoxy-3,7-dimethyl-2,6-octadiene, phenylacetaldehyde, rose oxide, ethyl-2-methylpentanoate, 1-(2,6,6-trimethyl-1,3-cyclohexadien-1-yl)-2-buten-1-one, ethyl vanillin, 2,6-dimethyl-2-octenol, 3,7-dimethyl-2-octenol, tert-butylcyclohexyl acetate, anisyl acetate, allyl cyclohexyloxyacetate, ethyllinalool, eugenol, coumarin, ethyl acetoacetate, 4-phenyl-2,4,6-trimethyl-1,3-dioxane, 4-methylene-3,5,6,6-tetramethyl-2-heptanone, ethyl tetrahydrosafranate, geranyl nitrile, cis-3-hexen-1-ol, cis-3-hexenyl acetate, cis-3-hexenyl methyl carbonate, 2,6-dimethyl-5-hepten-1-al, 4-(tricyclo[5.2.1.0]decylidene)-8-butanal, 5-(2,2,3-trimethyl-3-cyclopentenyl)-3-methylpentan-2-ol, p-tert-butyl-alpha-methylhydrocinnamaldehyde, ethyl[5.2.1.0]tricyclodecanecarboxylate, geraniol, citronellol, citral, linalool, linalyl acetate, ionone, phenylethanol and mixtures thereof.

For the purposes of the present invention, a volatile odorous substance preferably has a boiling point or boiling range below 300° C. The odorous substance is more preferably a readily volatile compound or mixture. The odorous substance particularly preferably has a boiling point or boiling range below 250° C., more preferably below 230° C., particularly preferably below 200° C.

Preference is likewise given to odorous substances which have a high volatility. The vapor pressure can be employed as a measure of the volatility. For the purposes of the present invention, a volatile odorous substance preferably has a vapor pressure of more than 0.001 kPa (20° C.). The odorous substance is more preferably a readily volatile compound or mixture. The odorous substance particularly preferably has a vapor pressure of more than 0.01 kPa (20° C.), more preferably a vapor pressure of more than 0.05 kPa (20° C.). Particular preference is given to the odorous substances having a vapor pressure of more than 0.1 kPa (20° C.).

An example in which a chemical reaction can take place in the presence of the metal organic framework of the invention is the alkoxylation of monools or polyols. The procedure for carrying out such alkoxylations is described in WO-A 03/035717 and WO-A 2005/03069. The porous metal organic framework of the invention can likewise be used for epoxidation and for preparing polyalkylene carbonates and hydrogen peroxide. Such reactions are described in WO-A 03/101975, WO-A 2004/037895 and US-A 2004/081611.

Particular preference is given to catalytic reactions.

Furthermore, the metal organic framework of the invention can serve as support, in particular as support for a catalyst.

EXAMPLES

Example 1

Preparation of a Pure Al-Fumarate Metal Organic Framework (MOF)

17.91 g of $AlCl_3 \cdot 6H_2O$ and 9.04 g of fumaric acid (Linker:Al ratio=1.05 mol/mol) are suspended in 550 ml of DMF (solids content=0.05 g/g) in a glass flask and stirred under reflux (130° C.) for 17 hours. The solid formed is filtered off and washed with 3×100 ml of acetone and 2×100 ml of methanol. The filtration time is less than 30 seconds.

The substance is subsequently dried at 100° C. in a vacuum drying oven for 16 hours. This gave 11.4 g of a white preproduct. The $N_2$ surface area is measured as 1155 m²/g (Langmuir).

Example 2

Preparation of a Pure Al-Fumarate MOF 17.91 g of $AlCl_3 \cdot 6H_2O$ and 10.34 g of fumaric acid (Al:Linker ratio=1.2 mol/mol) are suspended in 550 ml of DMF (solids content=0.051 g/g) in a glass flask and stirred under reflux (130° C.) for 17 hours. The solid formed is filtered off and washed with 3×100 ml of acetone and 2×100 ml of methanol. The substance is subsequently dried at 100° C. in a vacuum drying oven for 16 hours. This gave 11.4 g of a white preproduct. The $N_2$ surface area is measured as 1149 m$^2$/g (Langmuir).

Example 3

Preparation of a Pure Al-Fumarate MOF 17.91 g of AlCl$_3$*6H$_2$O and 14.64 g of fumaric acid (Al:Linker ratio=1.7 mol/mol) are suspended in 550 ml of DMF (solids content=0.058 g/g) in a glass flask and stirred under reflux (130° C.) for 17 hours. The solid formed is filtered off and washed with 3×100 ml of acetone and 2×100 ml of methanol. The substance is subsequently dried at 100° C. in a vacuum drying oven for 16 hours. This gave 11.4 g of a white preproduct. The $N_2$ surface area is measured as 1271 m$^2$/g (Langmuir).

Example 4

Preparation of a Pure Al-Fumarate MOF 26.9 g of AlCl$_3$*6H$_2$O and 15.4 g of fumaric acid (Linker:Al ratio=1.2 mol/mol) are suspended in 550 ml of DMF (solids content=0.078 g/g) in a glass flask and stirred under reflux (130° C.) for 96 hours. The solid formed is filtered off and washed with 3×100 ml of acetone and 3×100 ml of methanol. The substance is subsequently dried at 100° C. in a vacuum drying oven for 16 hours. This gave 18.4 g of a white preproduct. The $N_2$ surface area is measured as 1272 m$^2$/g (Langmuir).

Example 5

Hydrogen Isotherms at 77 K

Figure 2:
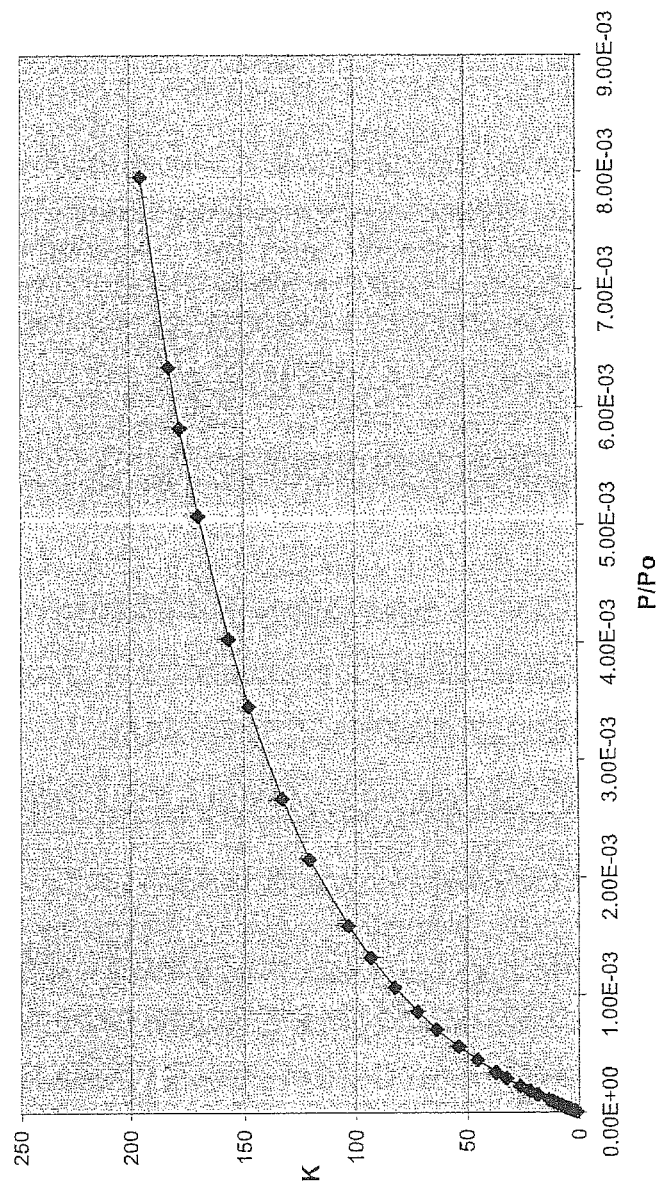
FIG. 2 shows the hydrogen capacity K (cc/g at STP) as a function of the relative pressure $p/p_o$ ($p_o$=94632.4 torr).

FIG. 2 shows the $H_2$ uptake of the MOF according to the invention. The measurement is carried out on a commercially available Autosorb-1 instrument from Quantachrome. The measurement temperature is 77.4 K. The sample is pretreated under reduced pressure for 4 hours at room temperature and subsequently for a further 4 hours at 200° C. before the measurement.

FIG. 2 shows the hydrogen capacity K (cc/g at STP) as a function of the relative pressure p/p$_o$ (p$_o$=94632.4 torr).

Example 6

Hydrogen Isotherms at 77 K

Figure 3:
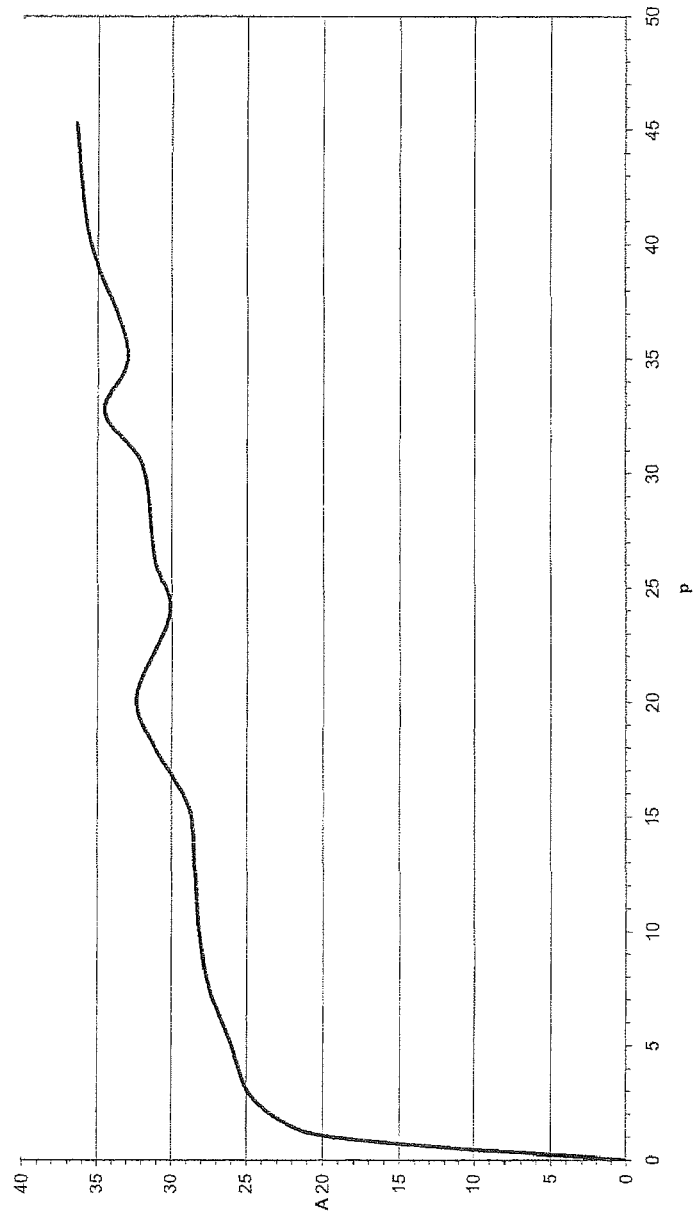
FIG. 3 shows the $H_2$ uptake of the Al-fumarate MOF. The measurement temperature is 77.4 K.

FIG. 3 shows the $H_2$ uptake of the Al-fumarate MOF. The measurement temperature is 77.4 K. The samples are each pretreated under reduced pressure for 4 hours at room temperature and subsequently for a further 4 hours at 200° C. before the measurement.

The hydrogen uptake (g/l) is shown as a function of the absolute pressure p (bar).

Example 7

Suitability for $CO_2$ Separations

Figure 4:
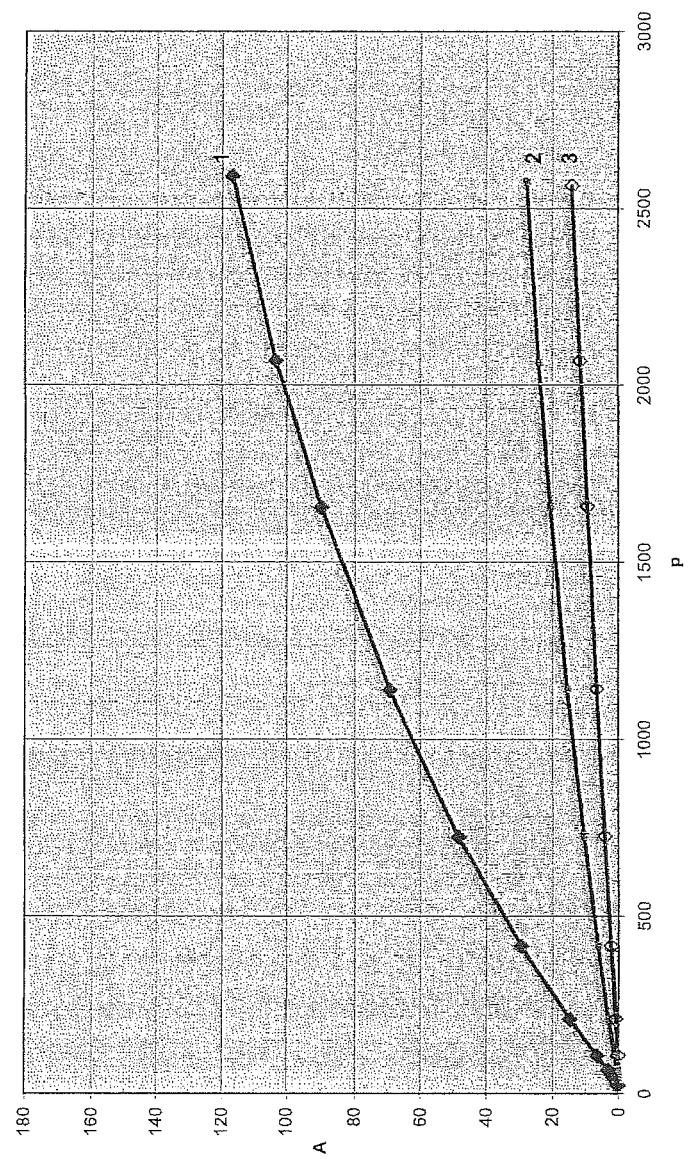
FIG. 4 shows the amount absorbed A (mg/g) as a function of the absolute pressure p (mbar). Here, the curves 1, 2 and 3 correspond to the gases $CO_2$, methane and CO.

Pure substance isotherms are recorded at 42° C. for absorption of $CO_2$, CO and methane (21° C.) on the material from example 1 (FIG. 4). The large difference between the CO uptake and the $CO_2$ uptake shows that this material in principle has a good selectivity for the separation tasks $CO_2$/methane and $CO_2$/CO.

FIG. 4 shows the amount absorbed A (mg/g) as a function of the absolute pressure p (mbar). Here, the curves 1, 2 and 3 correspond to the gases $CO_2$, methane and CO.

The invention claimed is:

1. A method comprising
   (i) providing a porous metal organic framework formed by Al$^{III}$ ions to which fumarate ions are coordinated to produce a framework structure,
   (ii) bringing a substance into contact with the metal organic framework such that the substance is uptaken by the porous metal organic framework to provide separation of the substance wherein the substance is a liquid, and wherein the liquid is a disinfectant, an inorganic or organic solvent, a fuel, a hydraulic fluid, a radiator fluid, a brake fluid or an oil or a mixture thereof.

2. The method of claim 1, wherein the X-ray diffraction pattern (XRD) of the framework has a basic reflection in the range 8°<2θ<12°.

3. The method of claim 1, wherein the framework has an orthorhombic one-dimensional channel structure.

4. The method of claim 1, wherein the framework as powder has a specific surface area determined according to the Langmuir method by $N_2$ adsorption at 77 K of at least 1000 m$^2$/g.

5. A method comprising
   (i) providing a porous metal organic framework formed by Al$^{III}$ ions to which fumarate ions are coordinated to produce a framework structure,
   (ii) bringing a substance into contact with the metal organic framework such that the substance is uptaken by the porous metal organic framework to provide separation of the substance wherein the substance is a liquid, and wherein the liquid is acetone, acetonitrile, aniline, anisole, benzene, benzonitrile, bromobenzene, butanol, tert-butanol, quinoline, chlorobenzene, chloroform, cyclohexane, diethylene glycol, diethyl ether, dimethylacetamide, dimethylformamide, dimethyl sulfoxide, dioxane, glacial acetic acid, acetic anhydride, ethyl acetate, ethanol, ethylene carbonate, ethylene dichloride, ethylene glycol, ethylene glycol dimethyl ether, formamide, hexane, isopropanol, methanol, methoxypropanol, 3-methyl-1-butanol, methylene chloride, methyl ethyl ketone, N-methylformamide, N-methylpyrrolidone, nitrobenzene, nitromethane, piperidine, propanol, propylene carbonate, pyridine, carbon disulfide, sulfolane, tetrachloroethene, carbon tetrachloride, tetrahydrofuran, toluene, 1,1,1-trichloroethane, trichloroethylene, triethylamine, triethylene glycol, triglyme, water or a mixture thereof.

* * * * *